United States Patent [19]

Meyer et al.

[11] Patent Number: 4,741,737

[45] Date of Patent: May 3, 1988

[54] PREFILLED AMPOULE-SYRINGE

[75] Inventors: Gabriel Meyer; Ernst Howald, both of Vesenaz, Switzerland

[73] Assignee: Medicorp Holding S.A., Luxembourg

[21] Appl. No.: 914,350

[22] Filed: Oct. 2, 1986

Related U.S. Application Data

[63] Continuation-in-part of Ser. No. 561,057, Dec. 13, 1983, abandoned.

[30] Foreign Application Priority Data

Dec. 20, 1982 [WO] World Int. Prop. O. ............... PCT/CH82/00134

[51] Int. Cl.$^4$ .............................. A61M 37/00
[52] U.S. Cl. .................... 604/140; 604/146; 604/231; 604/238; 604/241
[58] Field of Search ............ 604/140, 146, 148, 231, 604/236, 238, 240, 241, 243, 89–91; 128/760, 763

[56] References Cited

U.S. PATENT DOCUMENTS

| | | | |
|---|---|---|---|
| 977,952 | 12/1910 | Hielman et al. | 604/231 |
| 1,139,720 | 5/1915 | Reed | 604/236 |
| 2,524,363 | 10/1950 | Smith | 604/231 |
| 3,159,159 | 12/1964 | Cohen | 604/236 |
| 3,563,415 | 2/1971 | Ogle | 604/231 |
| 3,722,512 | 3/1973 | Hein et al. | 604/231 |

FOREIGN PATENT DOCUMENTS

| | | | |
|---|---|---|---|
| 1441390 | 11/1968 | Fed. Rep. of Germany | 604/236 |
| 0334207 | 12/1903 | France | 604/231 |
| 0844179 | 7/1939 | France | 604/231 |

Primary Examiner—C. Fred Rosenbaum
Assistant Examiner—Mario Costantino
Attorney, Agent, or Firm—Hayes, Davis & Soloway

[57] ABSTRACT

A prefilled ampoule-syringe including an ampoule body having a smaller inner dimension than the body and a stopper means associated with an external capsule for closing the ampoule. The stopper is provided with an internal conduit having at least one transverse branch opening into a longitudinal branch between the interior of the capsule body and a needle-holding tip. The capsule is arranged for actual movement from a position within the neck where it is in a closed position to an open injection position within the ampoule body. When the capsule is in the position in the neck of the ampoule, the contents of the ampoule are in contact only with the walls of the ampoule and the inner surface of the stopper which faces into the neck. When the stopper is moved to injection position, the contents of the ampoule pass through the transverse passage and down the longitudinal passage to the needle holding tip for injection into a patient.

8 Claims, 1 Drawing Sheet

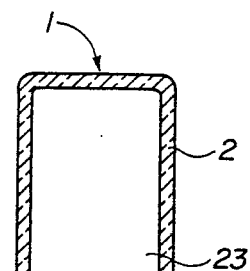
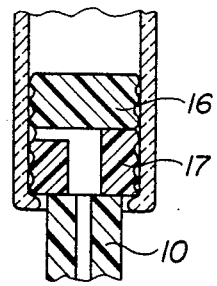
FIG. 3    FIG. 4
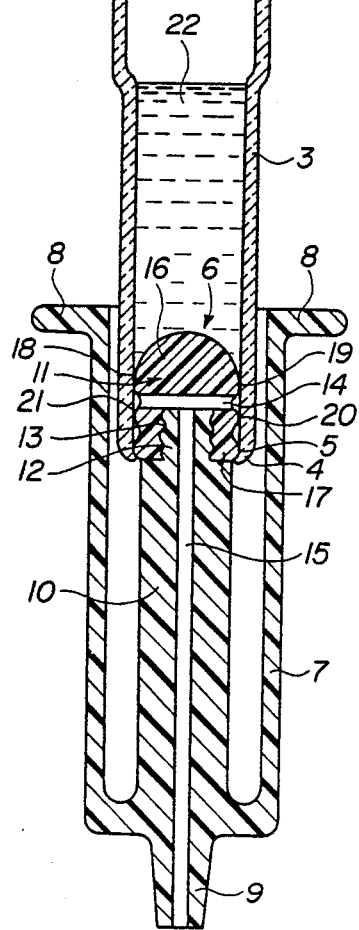
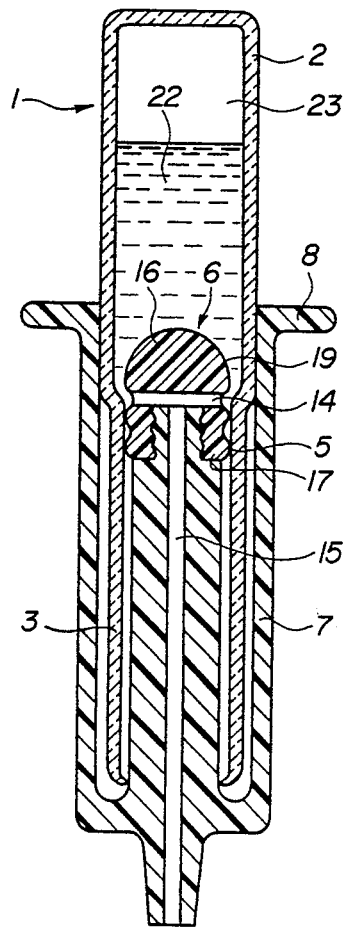
FIG. 1    FIG. 2

PREFILLED AMPOULE-SYRINGE

This application is a continuation-in-part of U.S. application Ser. No. 561,057 filed Dec. 13, 1983, which is now abandoned.

The present invention relates to a prefilled ampoule-syringe containing a liquid medication and a gas and comprising an ampoule body having an open end and a neck loacted near said open end, this neck having smaller transverse inner dimensions than said body and a stopper means associated with an external capsule. The stopper means is provided with an internal conduit having at least one transverse branch opening into a longitudinal branch for communication of the interior of the ampoule body with a needle-holding tip. The stopper means is arranged for movement within from a closed storage position to an open injection position.

Syringe-ampoules are already known in the art, particularly those described in French Patent No. 714,018. These devices are comprised of an ampoule containing a liquid medication and a gas under pressure, this ampoule being provided with a stopper encased by the open end of the ampoule, and associated with a rotatable valve traversed by an axial conduit, connected to a radial conduit designed to open into a cavity in communication with the interior of the ampoule. The embodiments illustrated by FIGS. 1 and 2 are not useful in practice since the operator has only one hand available to hold the syringe and to activate the valve, his other hand being occupied holding the patient's skin.

The embodiment of FIG. 3, which demonstrates a solution to this problem, is very costly and unsatisfactory in numerous aspects. Actually, this construction entails a stopper which is in contact with the pharmaceutical substance or liquid medication contained in the ampoule, a rotatable valve contained in a central opening disposed in the stopper means and also in partial contact with the substance to be injected, a special needle-holding cap adapted to the stopper means and a spiral spring between the stopper and the cap.

The manufacture of a special needle and needle holder is a costly operation. The fact that the needle is mounted on a needle-holding tip at the time of assembly and especially at the time the ampoule is pressurized means that the pressurized gas to be introduced into the ampoule must be injected through the syringe, thereby necessitating a complicated mechanism to avoid damaging the needle. This could also be achieved by filling the ampoule in a pressurized room or container, but the operation is complicated and relatively high cost. The pressurization of the pharmaceutical substance could be accomplished by injecting the gas through the needle-holding tip, previously positioned, followed by soldering or gluing the needle. Manipulating the needle is costly because it necessitates the utmost precautions. It must be done under sterile conditions to exclude any contamination, particularly glue residue.

The pharmaceutical substance is in contact with three elements made of different materials, the ampoule, the stopper and the valve. Furthermore, water-tightness between the stopper and the valve is difficult to achieve unless the body of the valve is firmly attached to the interior of the stopper, thereby causing considerable pull which impedes retraction of the ampoule at the time of injection.

Maintaining the stopper in place necessitates the use of an encasing ring. The elements comprising the stopper means for the ampoule are the following: a stopper, a valve situated in a cylindrical cavity of said stopper, an encasing ring, a needle-holding cap, a spring and a needle. Manufacturing and assembling all these pieces is extremely costly. Furthermore, preparation of the syringe for use requires the following operations: filling the ampoule with the pharmaceutical substance, placing the stopper on the ampoule, affixing the stopper by means of the encasing ring, positioning the valve in the central opening of the stopper, positioning the spring, injecting compressed gas into the ampoule to pressurize the liquid and affixing the needle. The various preparatory phases are both delicate and costly.

Furthermore, it is not guaranteed that the overpressure which is absolutely necessary for permitting injection of the liquid medication will remain in the ampoule after a relatively long storage period. Thus, if encasing of the container is not perfect, the pressurization will escape and the syringe can no longer be used.

Furthermore, it is known from the article which appears on page 17 of "Recipients en matiere plastique pour les preparations pharmaceutiques, essai et controle" ("Plastic Containers for Pharmaceutical Preparations, Experiments and Control"), published in 1974 by the World Health Organization, by Jack Cooper, that composite containers are often susceptible to interaction of materials. In particular, there has been observed a migration of certain components of synthetic material into pharmaceutical substance contents. Interaction between the pharmaceutical substance contents and the container when the latter is made of a polymer may change the physical characteristics of the polymer and/or pharmacological characteristics of the pharmaceuticals substance contents. Even if its characteristics are initially satisfactory, the changes which may occur as a result of the prolonged interaction oblige manufacturers to pay particular attention to stability during storage.

Another similar device is disclosed in U.S. Pat. No. 3,159,159, which can also be used as a prefilled syringe, comprising a valve system for dispensing a liquid medication, which is maintained under pressure in an adequate ampoule. The valve system functions like a stopper during a storage phase and like a spring actuated valve during the injection phase. The construction is complicated and the liquid is in contact with at least three different materials. In fact, this device presents all the drawbacks of the syringe disclosed in the French Patent.

The present invention proposes to overcome the various foregoing disadvantages and to offer the health profession a useful instrument, easy to manipulate, of economical construction and providing the patient with the requisite hygiene and cleanliness.

The main object of the invention is to realize a prefilled ampoule-syringe containing a liquid medication and a gas and comprising an ampoule with an ampoule body having a single open end and a neck located near said single open end, this neck having smaller transverse inner dimensions than said body, and a stopper means associated with an external capsule. The stopper means is provided with an internal conduit having at least one transverse branch opening into a longitudinal branch for communication of the interior of the ampoule body with a needle-holding tip. The stopper means is arranged for axial movement within said neck from a closed storage position, the axial movement producing a reduction of the inner volume of the ampoule body and inducing an overpressure of said gas. During this axial movement the stopper means penetrates at least partly within the ampoule body to an open injection position. The stopper means comprises a stopper body having an upper part located above said transverse branch and a lower part located below said transverse branch, and a rod element for cooperating at least with said lower part of said stopper body, said rod element being solidly attached to said external capsule. The upper part of said stopper body is provided with at least one continuous annular surface having larger transverse outer dimensions than the transverse inner dimensions of said ampoule neck so as to be in a compressed condition in said closed storage position. In the storage position the stopper body sealingly engages in direct contact with the inner wall of said neck and also during said axial movement so as to prevent flow of liquid from the ampoule body to said transverse branch. The stopper body has at least partly smaller transverse outer dimensions than the transverse inner dimensions of said ampoule body, so as to be in at least a partly expanded condition in said open injection position. The stopper body is at least partly disengaged from the inner wall of said ampoule body in the open injection position, so as to permit flow of liquid from the ampoule body to said transverse branch due to the overpressure of said gas. The said lower part of said stopper body is provided with at least one continuous annular surface having larger transverse outer dimensions than the transverse inner dimensions of said ampoule neck so as to be in a compressed condition in said open injection position, and being sealingly engaged in direct contact with said inner wall of said neck in said open injection position, so as to prevent flow of liquid from the interior of the ampoule body to the end opening of the neck. The axial distance between said transverse branch and the zone where the rod element is attached to the external capsule is substantially equal to the axial length of said neck.

According to a first embodiment of the invention, the upper and the lower parts of the stopper body are integral.

According to another embodiment of the invention, the upper and the lower parts of the stopper body are separate elements.

According to a further embodiment of the ampoule-syringe of the invention, said lower part of said stopper body is attached to said rod element.

According to another embodiment of the invention, said lower part of said stopper body is separated from said rod element.

The continuous annular peripheral surfaces of both said upper and said lower parts of said stopper body can be provided with at least one ring-shaped rim.

The present invention, its characteristics and principal advantages will be better understood with reference to the description of embodiments thereof and to the attached drawings, in which:

FIG. 1 is an axial section of a first embodiment of the prefilled ampoule-syringe of the invention, in which said stopper means is in the closed storage position.

FIG. 2 is a similar view in which said stopper means is in the open injection position.

FIG. 3 is a partial axial section of a second embodiment of the ampoule-syringe according to the invention, in which the stopper body is comprised of two separate parts; and FIG. 4 is a partial axial section of a third embodiment of the ampoule-syringe according to the invention, in which the stopper body is not attached to the rod element.

The prefilled ampoule-syringe according to FIGS. 1 and 2 comprises an ampoule 1 provided with an ampoule body 2 and a neck 3 of smaller transverse inner dimensions than said body. In a preferred embodiment the ampoule body and the neck have both a cylindrical shape and both inner and outer transverse dimensions of the neck are smaller than the outer diameter of said ampoule body. Neck 3 is provided with an opening which is the only opening of the ampoule. For some special applications the ampoule body 2 could be provided with a fixed stopper located at its end opposed to the neck. Neck 3 is provided with an annular rim 4 cooperating with an annular protruding rim 5 of the stopper means 6 for preventing the same from being pushed out of the neck 3 during the closed storage position.

An external capsule 7 is adapted to the neck 3 of ampoule 1. It is made of a relatively rigid plastic material and is provided with at least two diametrically opposed projections 8 forming two finger grips, and with a conical injection device holder tip 9.

In the embodiment represented by FIGS. 1 and 2, capsule 7 is integral with a rod element 10 made of the same relatively rigid plastic material. A stopper body 11 is mounted on the free end of the rod element 10, this assembly forming said stopper means 6. Rod element 10 is therefore provided with a tip 12 which engages into a complementary shaped cavity 13 located centrally in the stopper body 11.

The stopper means is provided with an internal conduit for permitting communication between the interior of the ampoule body with the injection device (not shown), i.e., a needle, during the injection phase. This internal conduit comprises at least one transverse branch 14 located in the stopper body 11 and an axial branch 15 located in the rod element 10. The stopper body is composed of an upper part 16 located above the transverse branch 14 and a lower part 17 located below the transverse branch 14. The upper part 16 of the stopper body is provided with a continuous annular surface 18, having the shape of an annular rim 19, the outer dimensions of which being greater than the inner diameter of the neck 3, so as to be in a compressed condition during the storage phase and during the axial displacement in the neck for bringing said stopper means from said closed storage position into said open injection position, and to be sealingly in direct contact with the inner wall of said neck. The lower part 17 of the stopper body is also provided with a continuous annular surface 20, having the shape of at least one annular rim 21, the outer dimensions of which being greater than the inner diameter of the neck 3, so as to be in a compressed condition during both the storage and the injection phase and to be sealingly in direct contact with the inner wall of said neck.

As represented by FIGS. 1 and 2, the ampoule 1 has a particularly long neck 3. During the storage phase, the stopper body occupies the closed storage position represented by FIG. 1; it is located near the end opening of the neck 3.

Since the continuous annular surface 18 of the upper part 16 of the stopper body is sealingly in direct contact with the wall of the neck, the liquid medication 22 contained in the ampoule body is prevented from flowing to the end openings of the transverse branch 14. The upper part 16 has the function of a sealing member during the storage phase. A gas 23 surmounts the liquid 22. The pressure of this gas is substantially equal to the atmospheric pressure during the storage phase.

For bringing the syringe from the storage condition into the injection condition, the latter being represented by FIG. 2, the user pushes the ampoule 1 into the direction of the external capsule 7. Since the stopper means is integral with or attached to the capsule, the stopper body penetrates into the neck 3 in direction of the ampoule body. This displacement produces a reduction of the inner volume of the ampoule body and induces an overpressure of the gas contained in the ampoule body. The pressure of the gas 23 increases as long as the upper part 16 of the stopper body 11 remains inside the neck 3.

At the moment when the upper part 16 penetrates into the ampoule body, it expands. The outer dimensions of said continuous annular surface 18 are smaller than the inner diameter of the ampoule body, so that liquid medication is allowed to flow to the transverse branch 14. Due to the overpressure surmounting the liquid, it is forced into the transverse branch and into the axial branch in direction of the injection device.

Since the lower part 17 of the stopper body is provided with a continuous annular surface which remains in the neck and is in a compressed condition, the liquid cannot escape in direction of the neck end opening. The length of the neck is preferably determined to be sufficient to induce a high enough overpressure to permit evacuation of all the liquid contained in the ampoule. The increase of the pressure of the gas is preferably just sufficient to inject the whole dose of liquid. If the pressure is too low, the liquid cannot be completely injected. If the pressure is too high, there is a risk of injecting gas bubbles into the patient's body.

An adequate axial displacement permits obtaining the required overpressure.

FIG. 3 shows a device in which stopper body 6 is comprised of an upper part 16 and a lower part 17 which are two separate elements.

FIG. 4 shows a device in which stopper body 6 is also composed of an upper part 16 which is separated from the lower part 17. Furthermore, rod element 10 is not attached to the lower part 17 of the stopper body.

The main advantage of the syringe according to the invention is to create an extempore overpressure injection device at the moment when it is needed without using any external equipment.

In some prior art systems, the overpressure is introduced in the ampoule during or after the filling-up phase. Such an operation needs complicated installations and is expensive. Further, it is impossible to guarantee that the overpressure does not escape during the storage phase which can extend from some months to some years. In some other prior art systems, the overpressure is introduced by an external source just before use of the syringe. Such an operation needs a special preparation and adequate devices.

The present invention has the advantage of storage without overpressure and inducing the overpressure just before use without any special device such as an external pressure source.

We claim:

1. Prefilled ampoule-syringe containing a liquid medication and a gas and comprising an ampoule with an ampoule body having a single open end and a neck located near said single open end, this neck having smaller transverse inner dimensions than said body, and a stopper means comprising a stopper body having an upper part communicating with said ampoule and a lower part communicating with a rod element, said rod element being formed integrally with an external capsule, said stopper means being provided with an internal conduit means having at least one transverse branch and a longitudinal branch in fluid communication with the transverse branch for communication of the interior of the ampoule body with a needle holding tip when in an open position, said stopper body being located within said neck of the ampoule and axially movable from a closed to an open position, said axial movement producing a reduction of the inner volume of the ampoule body and inducing an overpressure of said gas, said upper part of said stopper body is provided with at least one continuous annular surface having larger transverse outer dimensions than the transverse inner dimensions of said ampoule neck so as to be in a compressed condition and sealingly engaged in direct contact with the inner wall of said neck in said closed position and during said axial movement so as to prevent flow of liquid from the ampoule body to said transverse branch, and having at least partly smaller transverse outer dimensions than the transverse inner dimensions of said ampoule body so as to be in at least a partly expanded condition in said open position, and being at least partly disengaged from the inner wall of said ampoule body in said open position so as to permit flow of the liquid medication from the ampoule body to said transverse branch due to said overpressure of said gas, and the axial distance between said transverse branch and the zone where the rod element is attached to the external capsule being substantially equal to the axial length of said neck.

2. Prefilled ampoule-syringe according to claim 1, in which said upper part and said lower part of said stopper body are integral.

3. Prefilled ampoule-syringe according to claim 1, in which said upper part and said lower part of said stopper body are separate elements.

4. Prefilled ampoule-syringe according to claim 1, in which said lower part is attached to said rod element.

5. Prefilled ampoule-syringe according to claim 1, in which said lower part is separably attached to said rod element.

6. Prefilled ampoule-syringe according to claim 1, in which said continuous annular surface of said upper part of said stopper body is provided with at least one ring-shaped rim.

7. Prefilled ampoule-syringe according to claim 1, in which said continuous annular surface of said lower part of said stopper body is provided with at least one ring-shaped rim.

8. Prefilled ampoule-syringe according to claim 7 in which the lower part of the ampoule neck has a reduced diameter which is smaller than the diameter of the ring shaped rim on the lower part of the stopper body.

* * * * *